United States Patent [19]

Herms et al.

[11] Patent Number: 5,597,552
[45] Date of Patent: Jan. 28, 1997

[54] DENTINAL DESENSITIZING COMPOSITIONS

[75] Inventors: James K. Herms, Jersey City; Kenneth J. Markowitz, Fanwood, both of N.J.

[73] Assignee: Block Drug Company Inc., Jersey City, N.J.

[21] Appl. No.: 167,558

[22] Filed: Dec. 14, 1993

Related U.S. Application Data

[63] Continuation-in-part of Ser. No. 811,811, Dec. 20, 1991, Pat. No. 5,270,031.

[51] Int. Cl.$^6$ ............ A61K 7/16; A61K 31/315; A61K 33/30; A61K 31/78
[52] U.S. Cl. ............ 424/49; 424/641; 424/642; 424/643
[58] Field of Search ............ 424/49–58

[56] References Cited

U.S. PATENT DOCUMENTS

| | | | |
|---|---|---|---|
| 2,975,102 | 3/1961 | Matsumura et al. | 167/93 |
| 3,003,988 | 10/1961 | Germann et al. | 260/33.6 |
| 3,122,483 | 2/1964 | Rosenthal | 167/93 |
| 3,325,368 | 6/1967 | Wood | 167/93 |
| 3,772,431 | 11/1973 | Mlkvy | 424/44 |
| 3,863,006 | 1/1975 | Hodosh | 424/49 |
| 3,888,976 | 6/1975 | Mlkvy | 424/49 |
| 4,138,477 | 2/1979 | Gaffar | 424/52 |
| 4,296,096 | 10/1981 | Pierce | 424/52 |
| 4,343,608 | 8/1982 | Hodosh | 423/224 |
| 4,407,675 | 10/1983 | Hodosh | 106/35 |
| 4,758,630 | 7/1988 | Shah et al. | 525/207 |
| 5,013,541 | 5/1991 | Elliott et al. | 424/49 |
| 5,073,604 | 12/1991 | Huleva et al. | 525/327.8 |
| 5,178,869 | 1/1993 | Ebine et al. | 424/49 |
| 5,188,818 | 2/1993 | Merianos et al. | 424/49 |
| 5,211,939 | 5/1993 | Turesky et al. | 424/49 |
| 5,234,971 | 8/1993 | Imai et al. | 523/113 |
| 5,240,569 | 8/1993 | Norfleet et al. | 424/52 |
| 5,240,697 | 8/1993 | Norfleet et al. | 424/52 |
| 5,250,288 | 10/1993 | Turesky et al. | 424/49 |
| 5,270,031 | 12/1993 | Lim et al. | 424/49 |
| 5,328,682 | 7/1994 | Pullen et al. | 424/49 |

FOREIGN PATENT DOCUMENTS

| | | |
|---|---|---|
| 200508 | 12/1986 | European Pat. Off. . |
| 549281 | 6/1993 | European Pat. Off. . |
| 2670383 | 6/1992 | France . |
| 2239601 | 7/1991 | United Kingdom . |

OTHER PUBLICATIONS

Mason et al Clinical Prevention Denstr, vol. 12 No. 6:6–12 Jan. 1991 Evaluation of Tartar Control Dentifrices in In Vitro Models of Dentin Sensitivity.

*Primary Examiner*—Shep K. Rose
*Attorney, Agent, or Firm*—Ostrolenk, Faber, Gerb & Soffen, LLP

[57] ABSTRACT

A composition containing a water soluble or water swellable polyelectrolyte mixed salt in a dentifrice base or other oral compositions which can be used for relieving pain and discomfort caused by hypersensitive teeth.

14 Claims, No Drawings

DENTINAL DESENSITIZING COMPOSITIONS

BACKGROUND OF THE INVENTION

This is a continuation-in-part of application Ser. No. 07/811,811, filed Dec. 20, 1991, and now U.S. Pat. No. 5,270,031.

Hypersensitive teeth can cause pain and discomfort when subjected to changes in temperature, pressure, or chemical action. Exposure of the dentin frequently leads to hypersensitivity. Dentin exposure may occur due to recession of the gums, periodontal disease and improper dental care. The usual method of treating hypersensitive teeth employs a desensitizing dentifrice or solution. Some of the active ingredients used in desensitizing dentifrices include strontium chloride, strontium acetate, potassium nitrate, and potassium chloride. Other treatments are applied professionally as a solution. These include solutions of ferric oxalate or potassium oxalate.

One approach to desensitization is to occlude exposed dentinal tubules. Dentinal tubules lead from the pulp to the surface of the dentin. When the surface of the tooth is eroded, the dentinal tubules become exposed to the external environment. The exposed dentinal tubules provide a pathway for transmission of fluid flow to the pulpal nerves and this is induced by changes in temperature, pressure and ionic gradients. By blocking the tubules, the external stimuli have a diminished effect, and less pain will be felt.

Some active ingredients, such as ferric oxalate, are known to form mineral deposits on the surfaces of exposed dentinal tubules, effectively blocking the openings. In some cases, the abrasive action from brushing may cause a smear layer to form over the surface of the tooth and thus plug up the open tubules. The accumulation of particulate matter from the interstitial fluid passing through the dentinal tubules or remineralization within the tubules can cause a natural occlusion of the tubules.

Nerve inactivation is another mechanism whereby desensitization can occur. This relies on the action of an active ingredient such as potassium nitrate on the nerves. By altering the ionic balance in the nerve, the threshold of nerve stimulation is increased. Thus a higher level of stimulation is needed to evoke a painful response.

The materials which have been used as active ingredients in the treatment of hypersensitive teeth are generally inorganic salts or hydrophobic compounds. Although hydrophilic polymers have been used in oral compositions as excipients or the like, they have not been suggested as being useful active ingredients for desensitization purposes. Most of the hydrophilic polymers have been used to control the viscosity of the oral formulation or to give it thixotropic properties.

An example of such a polymer is polyacrylic acid which is used as a thickener in dentifrice formulations. It has also been used in gels, mouthwashes and buccal adhesive patches. However, polyacrylic acid has also been used for other purposes. For example, Leonard et al. (U.S. Pat. No. 5,011,830) state an oral composition containing an alkali pyrophosphate salt, a fluoride salt and a polyacrylic acid or a copolymer of acrylic acid and another monomer can provide enhanced anti-calculus benefits. Gaffar (U.S. Pat. No. 3,956,480) uses an anionic polymer such as polyacrylic acid with chlorhexidine as an anti-calculus agent. Benedict and Sunberg (U.S. Pat. No. 4,661,341) describe the use of polyacrylic acid or copolymers of polyacrylic acid as anti-calculus agents. In none of the examples above or elsewhere, as far as we are aware, are these polymers claimed to provide a desensitizing effect.

It has now been determined that certain water soluble or water swellable polyelectrolytes, i.e. polymers with functional groups that are capable of bearing one or more charged groups in an aqueous solution have desensitizing properties.

It is accordingly the object of this invention to provide new dentinal desensitizing agents. This and other objects of the invention will become apparent to those skilled in this art from the following detailed description.

SUMMARY OF THE INVENTION

This invention relates to an oral composition and method which is useful for relieving pain and discomfort caused by hypersensitive teeth. More particularly, the invention relates to the use of certain water soluble or water swellable polyelectrolyte partial salts as a dental desensitization agent. The cations used to make the salt can include ammonium, alkylammonium, calcium, sodium, potassium, strontium, magnesium, zinc, aluminum, tin, iron, barium, lanthanum, titanium, bismuth and copper. The salts may contain single cations or mixed cations.

The polymer and its salts may be formulated into a dentifrice, gel, buccal adhesive patch, mouthwash, lozenge, or gum. Use of these oral compositions on a regular basis can provide relief from the pain and discomfort of hypersensitive teeth. The oral composition described above may also provide for a sustained release mode of action for the delivery of strontium or potassium ions from the water soluble or water swellable polyelectrolytes. The polyelectrolytes may also be used in conjunction with additional desensitizing agents such as strontium chloride or potassium nitrate in an oral composition. In addition a source of fluoride ion can be incorporated into the composition.

DESCRIPTION OF THE INVENTION

In accordance with the present invention, a water soluble or water swellable polyelectrolyte partial salt is used as a dentinal desensitizing agent. The agent can be incorporated into a dentifrice, gel, mouthwash, lozenge, buccal adhesive patch, gum or the like. The water soluble or swellable polymer is an acrylic acid polymer (which term includes acrylic acid copolymers). Polyacrylic acid can be obtained, for instance, from B. F. Goodrich under the tradename Carbopol® or Noveon® as a cross-linked polyacrylic acid generically catagorized as carbomer or polycarbophil. Polyacrylic acid can also be obtained from Rohm and Haas under the tradename Acusol™.

The commercially available polymers are produced over a range of molecular weights. Thus, for instance, Carbopol® and Noveon® are available in different grades with different rheological properties. The different grades range in molecular weight from 450,000 (907 type) to 4,000,000 (980 type). It is preferable to employ the highest molecular weight grade consistent with the viscosity of the formulation being prepared and concentration of the agent. The formulations will contain a desensitizing amount which is generally from about 0.1% to 30% by weight of the polymer partial salt, with about 1–15% being preferred and about 2–12% most preferred. For any given concentration, viscosity generally increases with molecular weight and for any given molecular weight, viscosity generally increases with concentration.

The properties of the polyacrylic acid are modified to obtain the most advantageous properties by partial neutralization. The cations may be present in the salts at about 20% to 100% equivalent mole ratio of the polymer. The preferred range is from about 40% to 90% equivalent of the polymer. The cations that can be used include ammonium, alkylammonium, calcium, sodium, potassium, strontium, zinc, aluminum, magnesium, tin, iron, barium, lanthanum, titanium, bismuth and copper. The cations can be used singly or as a mixture of different cations. These salts as such are well known in the art.

The salts of the polymer can be made by making a solution of the polymer in water and then adding ammonia or a metal salt such as the hydroxide, carbonate, bicarbonate, oxide, acetate, citrate, lactate, formate or phosphate. The metal salt is preferably alkaline. The solution is stirred, with heating if necessary, until the polymer has dissolved. It will usually have a pH between about 3.5 and 9, depending on the amount of metal salt used. The salt solution can be directly incorporated into an aqueous oral composition. Alternatively, the solution can be evaporated to dryness to give a solid salt which can be milled to a fine powder, if desired, and incorporated into an oral composition.

In order to modify the physical properties of the oral composition, it is preferred to utilize an alkali metal or ammonium salt of the polyelectrolyte partially substituted with 0,005 to 0.4, preferably 0,015 to 0.25, mole equivalent of calcium, zinc or other multivalent (divalent or polyvalent) cation. These cations may include but are not limited to zinc, tin, magnesium, strontium, copper, iron, bismuth, aluminum and bis(biguanidinium). Adding the cation in such a way as to favor intramolecular crosslinking can have the advantage of reducing the viscosity and hence improving the organoleptic characteristics of the oral composition without hindering the ability of the composition to reduce dentin fluid flow.

Oral compositions describing polyacrylate polymers partially substituted with multivalent metal salts have been described. Gaffar in U.S. Pat. No. 4,138,477 discloses the use of zinc polymer combinations formed by the reaction or interaction of zinc compound with an anionic polymer as oral compositions to control mouth odor. The purpose of that invention is to have the complex adhere to the tissues of the oral cavity where slow release of zinc occurs.

U.S. Pat. No. 4,296,096 to Pierce describes the preparation of a high viscosity dentifrice containing a polyelectrolyte polymer ionically crosslinked with aluminum or other polyvalent cation to form particles less than 74 microns in size. These particles act as a water absorbing insoluble gel and serve as a dentifrice humectant. Zinc is mentioned as one of the ionic crosslinking agents. The methods of ion-polymer mixing described would result in extensive intermolecular crosslinking of the polymer. In the present invention, zinc is added under conditions which would favor intramolecular crosslinking for the purpose of deswelling of the polyacrylic acid gel.

In order to obtain the desired physical properties the following general procedure has to be used to fabricate the partially substituted polyacrylic acid salt.

First a resin power is dispersed into an acidified aqueous solution containing the desired quantities of the divalent or polyvalent metal salt. Other desensitizing salts such as $KNO_3$ can be present in the acidified solution as well. After hydration of the resin is complete, a slurry of an abrasive may be added under high shear. The pH of the dispersion may be adjusted to the desired value by the rapid addition of an alkaline neutralizing agent under high shear. In order to obtain the desired physical properties it is important to raise the pH of the dispersion rapidly, e.g., at least four pH units per minute. Finally the foaming agent, fluoride, flavors and other desired ingredients are blended in.

The polymer salt can be formulated into a dentifrice, mouthwash, lozenge, buccal adhesive patch or gum using ingredients and procedures which are well known and commonly used in preparing these oral compositions. By way of example, without limitation, it is possible to incorporate a fluoride source into the oral composition. Of course, the ingredients used to make the above oral compositions should be compatible with the polymer and its salts. It is also possible to formulate the oral compositions in conjunction with additional desensitizing agents. Additional desensitizing agents include, without limitation, sodium fluoride, sodium silicofluoride, zinc chloride, formaldehyde, glycerin and silver nitrate. Additional desensitizing agents may also include potassium-containing compounds, such as potassium nitrate, as described in U.S. Pat. No. 3,863,006 and strontium-containing compounds, such as strontium chloride, as described in U.S. Pat. No. 3,122,483.

The polyacrylic acid partial salts have an affinity for the tooth surface and can maintain their presence over a period of time. This allows for a longer term availability of the actives for desensitization.

In order to further illustrate the present invention, various non-limiting examples are set forth below. In these examples, as throughout this specification and claims, all temperatures are in degrees centigrade and all parts and percentages are by weight unless otherwise indicated.

EXAMPLE 1

A gel containing a sodium (80% equivalent) salt of polyacrylic acid was prepared from the following ingredients:

| INGREDIENT | % WEIGHT |
|---|---|
| Polyacrylic Acid | 2.9% |
| Sodium hydroxide | 1.3% |
| Glycerin | 21.0% |
| Potassium Nitrate | 5.0% |
| Water | 69.6% |
| Sodium Fluoride | 0.2% |

EXAMPLE 2

A dentifrice containing 5% polyacrylic acid (85% equivalent sodium salt) was prepared from the following ingredients:

| INGREDIENT | % WEIGHT |
|---|---|
| Carbomer | 4.0% |
| Sodium hydroxide | 1.8% |
| Glycerin | 20.0% |
| Potassium Nitrate | 5.0% |
| Silica | 3.9% |
| Poloxamer 237 | 2.5% |
| Flavors & Preservatives | 0.7% |
| Water | 61.9% |
| Sodium Fluoride | 0.2% |

EXAMPLE 3

A mouthwash was made by mixing the following ingredients:

| INGREDIENT | % WEIGHT |
| --- | --- |
| Polyacrylic acid (Na/Zn salt) | 2.0% |
| Alcohol 190 Proof (Grain Alcohol) | 4.0% |
| Sorbitol | 10.0% |
| Poloxamer 407 | 2.0% |
| Flavor | 0.3% |
| Water | 81.7% |

EXAMPLE 4

A desensitizing gel dentifrice with fluoride was prepared from the following ingredients:

| Carbomer | 4.2% |
| --- | --- |
| Zinc sulfate | 0.7% |
| Hydrochloric acid, 37% | 0.2% |
| Potassium nitrate | 5.0% |
| Sodium hydroxide | 2.2% |
| Sodium fluoride | 0.2% |
| Glycerin | 20.0% |
| Hydrated silica | 5.0% |
| Poloxamer 237 | 2.5% |
| Flavors & preservatives | 1.5% |
| Water | 58.5% |

EXAMPLE 5

A desensitizing gel dentifrice with fluoride was prepared from the following ingredients:

| Polyacrylic acid | 4.0% |
| --- | --- |
| Zinc sulfate | 0.5% |
| Hydrochloric acid, 37% | 0.1% |
| Sodium hydroxide | 2.0% |
| Sodium fluoride | 0.2% |
| Glycerin | 20.0% |
| Hydrated silica | 4.0% |
| Cocamidopropyl betaine, 30% | 6.0% |
| Flavors & preservatives | 1.5% |
| Water | 61.7% |

EXAMPLE 6

A desensitizing paste dentifrice was prepared from the following ingredients:

| Polyacrylic acid | 4.2% |
| --- | --- |
| Zinc sulfate | 0.7% |
| Hydrochloric acid, 37% | 0.2% |
| Potassium nitrate | 5.0% |
| Sodium hydroxide | 2.2% |
| Sodium fluoride | 0.2% |
| Glycerin | 16.5% |
| Calcium pyrophosphate | 10.0% |
| Cocamidopropyl betaine, 30% | 7.0% |
| Flavors & preservatives | 1.5% |
| Water | 52.5% |

EXAMPLE 7

A desensitizing paste dentifrice was prepared from the following ingredients:

| Polycarbophil | 4.2% |
| --- | --- |
| Calcium chloride | 0.5% |
| Hydrochloric acid, 37% | 0.2% |
| Potassium chloride | 3.7% |
| Sodium hydroxide | 2.2% |
| Glycerin | 17.0% |
| Calcium pyrophosphate | 10.0% |
| Cocamidopropyl betaine, 30% | 7.0% |
| Flavors & preservatives | 1.5% |
| Water | 53.7% |

EXAMPLE 8

A desensitizing chewing gum was prepared from the following ingredients:

| Polyacrylic acid (sodium, zinc) salt | 1.5% |
| --- | --- |
| Potassium chloride | 1.6% |
| Sodium fluoride | 0.01% |
| Gum base | 40.0% |
| Lecithin | 0.5% |
| Flavor | 1.0% |
| Mannitol | 3.0% |
| Sorbitol | 52.39% |

EXAMPLE 9

A desensitizing oral lozenge was prepared from the following ingredients:

| Polyacrylic acid sodium salt | 1.5% |
| --- | --- |
| Zinc chloride | 0.1% |
| Sodium fluoride | 0.01% |
| Flavor | 0.5% |
| Sorbitol | 97.89% |

Tests Of Oral Compositions Of Examples

The prepared solutions and oral compositions were tested using the method described by Pashley (J. Periodontology, Vol. 55, No. 9, p. 522, September 1984). This test measures the flow of fluid through a sliced dentin disc. A treatment that will reduce the flow through the discs can also result in reduced dentinal hypersensitivity for people using the treatment.

A caries free tooth is sliced to obtain a 0.4 to 0.6 mm thick dentin disc. The disc is mounted in a split chamber device (J. Dent. Research 57:187, 1978). The initial flow of fluid through the disc is measured, and then the disc is treated by brushing with one of the desensitizing treatments. After brushing, the flow rate is again measured and the reduction in flow is calculated from these measurements. The following compositions were used and the reduction in flow is reported. The results for the dentifrices are based on 1 to 1 dilution with artificial or human saliva.

| Treatment | % Change in Flow |
| --- | --- |
| Example 1 | −48% |
| Example 2 | −63% |
| Example 4 | −97% |
| Example 7 | −80% |

Various changes and modifications can be made in the process and products of this invention without departing from the scope thereof. The various embodiments described herein were for the purpose of further illustrating the invention but were not intended to limit it.

What is claimed is:

1. In a gel or paste dentrifice containing a desensitizing amount of a desensitizing agent, the improvement which consists essentially of the desensitizing agent being at least one water soluble or water swellable alkali metal or ammonium salt of an acrylic acid polymer containing about 0,005–0.4 mole equivalent of zinc and in which the dentrifice does not contain an additional desensitizing agent, said desensitizing amount being sufficient to reduce dentinal fluid flow.

2. The dentrifice of claim 1 in which the amount of the member of the group is about 0.015 to 0.25 mole equivalent.

3. The dentrifice of claim 1 in which the alkali metal cation is sodium.

4. The dentrifice of claim 1 in which the amount of desensitizing agent is about 0.1 to 30% by weight of the composition.

5. The dentrifice of claim 4 in which the amount is about 1 to 15% by weight.

6. The dentrifice of claim 5 in which the amount is about 2 to 12% by weight.

7. In a method of desensitizing teeth by applying thereto a desensitizing amount of a dentrifice containing a desensitizing agent, the improvement which comprises employing the dentrifice of claim 1 as the dentrifice.

8. In a method of desensitizing teeth by applying thereto a desensitizing amount of a dentrifice containing a desensitizing agent, the improvement which comprises employing the dentrifice of claim 2 as the dentrifice.

9. In a method of desensitizing teeth by applying thereto a desensitizing amount of a dentrifice containing a desensitizing agent, the improvement which comprises employing the dentrifice of claim 3 as the dentrifice.

10. In a method of desensitizing teeth by applying thereto a desensitizing amount of a dentrifice containing a desensitizing agent, the improvement which comprises employing the dentrifice of claim 4 as the dentrifice.

11. In a method of desensitizing teeth by applying thereto a desensitizing amount of a dentrifice containing a desensitizing agent, the improvement which comprises employing the dentrifice of claim 5 as the dentrifice.

12. In a method of desensitizing teeth by applying thereto a desensitizing amount of a dentrifice containing a desensitizing agent, the improvement which comprises employing the dentrifice of claim 6 as the dentrifice.

13. The dentrifice of claim 2 in which the polymer is a cross-linked homopolymer having a molecular weight of 450,000 to 4,000,000 which is about 40–90% mole equivalently neutralized.

14. In a method of desensitizing teeth by applying thereto a desensitizing amount of a dentrifice containing a desensitizing agent, the improvement which comprises employing the dentrifice of claim 13 as the dentrifice.

* * * * *